United States Patent [19]

Nnadi et al.

[11] 4,113,725

[45] Sep. 12, 1978

[54] MULTIFUNCTIONAL ADDITIVES

[75] Inventors: John C. Nnadi, Glassboro; Israel J. Heilweil, Princeton, both of N.J.

[73] Assignee: Mobil Oil Corporation, New York, N.Y.

[21] Appl. No.: 564,954

[22] Filed: Apr. 3, 1975

Related U.S. Application Data

[63] Continuation-in-part of Ser. No. 248,226, Apr. 27, 1972, Pat. No. 3,888,773.

[51] Int. Cl.[2] .................. C07D 239/48; C07D 239/50; C07D 401/14; C07D 403/06

[52] U.S. Cl. .................................... 544/296; 544/323; 544/324; 544/357; 544/238; 544/295; 544/405; 544/336; 544/224; 544/330; 544/332; 544/212; 544/198; 544/329; 544/326; 544/328; 544/331; 252/47.5; 252/48.6; 252/49.9; 252/51.5 R; 260/296 R

[58] Field of Search ............... 260/249.6, 249.8, 249.5, 260/249.9, 256.4 R, 256.4 N, 250 AH, 250 A, 250 BN, 268 A, 268 B, 268 BI, 256.5 R, 268 R

[56] References Cited

U.S. PATENT DOCUMENTS

| | | | |
|---|---|---|---|
| 2,506,351 | 5/1950 | English et al. | 260/250 BN |
| 2,544,071 | 3/1951 | Dudley | 260/249.6 |
| 2,568,876 | 9/1951 | White et al. | 260/256.4 M |
| 3,055,896 | 9/1962 | Boyle et al. | 260/249.5 |
| 3,200,076 | 8/1965 | Anderson et al. | 260/268 PL |
| 3,206,407 | 9/1965 | Lutwack | 260/249.6 X |
| 3,278,428 | 10/1966 | Hedenburg et al. | 260/249.6 X |
| 3,301,823 | 1/1967 | Gehm et al. | 260/249.8 X |
| 3,308,101 | 3/1967 | Ikeda | 260/249.6 X |
| 3,309,345 | 3/1967 | Lutwack | 260/249.8 X |
| 3,310,557 | 3/1967 | Kleemann | 260/249.6 |
| 3,322,763 | 5/1967 | Dazzi et al. | 260/249.6 |
| 3,323,893 | 6/1967 | Reicheneder et al. | 260/250 AM |
| 3,515,603 | 6/1970 | Brown et al. | 260/249.6 X |
| 3,558,611 | 1/1971 | Fleck | 260/249.8 X |
| 3,575,705 | 4/1971 | Sato et al. | 260/249.6 X |
| 3,595,639 | 7/1971 | Mason et al. | 260/249.8 |
| 3,625,936 | 12/1971 | Meininger et al. | 260/249.8 X |
| 3,627,749 | 12/1971 | Ackermann et al. | 260/249.8 X |
| 3,642,720 | 2/1972 | Kray et al. | 260/249.8 X |
| 3,642,787 | 2/1972 | Ponzini et al. | 260/249.8 X |
| 3,734,909 | 5/1973 | Varsanyi et al. | 260/249.6 |
| 3,929,765 | 12/1975 | Suzuki et al. | 260/250 A |

OTHER PUBLICATIONS

Brown et al., "The Pyrimidines," Interscience Publishers, New York, (1962), p. 516.

*Primary Examiner*—John M. Ford
*Attorney, Agent, or Firm*—Charles A. Huggett; Malcolm Keen

[57] ABSTRACT

As a new class of multifunctional additives for industrial fluids, the compounds having the following general formula:

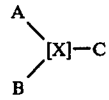

and (a)

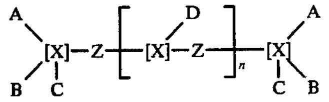

(b)

in which each X and Y represents a heterocyclic nitrogen radical and may be the same or different for each occurrence of X and Y; Z is a basic nitrogen-containing radical; *n* is 0 or an integer of at least 1, preferably 1 to 10; and A, B, C, and D are linked groups derived from compounds which may provide desired functions, such as detergent, antioxidant, and antiwear properties, or indirectly useful functions, such as adsorbency. At least one of A, B, C, or D is amino or anilino or is derived from an alkenylsuccinimide or an alkyl lactam or tetrahydropyrrolidine, or alkyl-substituted Mannich base, having at least 8 carbon atoms in the alkenyl or alkyl radical, or combinations of any of these. The reaction between these products and metal compounds particularly alkali and alkaline earth metal compounds provides more improved properties.

25 Claims, No Drawings

MULTIFUNCTIONAL ADDITIVES

CROSS-REFERENCE TO RELATED APPLICATIONS

This application is a continuation-in-part of application U.S. Ser. No. 248,226, filed on Apr. 27, 1972, now U.S. Pat. No. 3,888,773.

BACKGROUND OF THE INVENTION

1. Field of the Invention

This invention relates to novel additives for compositions and, in particular, it relates to hydrocarbon fluid compositions containing interlinked multifunctional additives.

2. Description of the Prior Art

In the U.S. Pat. Nos. 3,172,892 and 3,219,666 there are disclosed ashless additives derived from succinic acid compounds and polyamines; U.S. Pat. No. 3,024,195 discloses lubricating oil compositions containing alkenylsuccinimide N-alkylpiperazine; U.S. Pat. No. 3,200,076 discloses compounds of an alkenylsuccinic compound and a polypiperazinyl alkylene; and U.S. Pat. No. 3,455,386 describes polypropenylsuccinimide derivatives. U.S. Pat. No. 3,368,972 describes the preparation of Mannich bases. The compounds mentioned in these patents do not contain interlinked molecules. Although they have known utility as ashless detergents, they may not be effective, for example in lubricating oils for engines operating at high temperatures and pressures for long periods of time.

In U.S. Pat. Nos. 3,278,436 of Dazzi et al., 3,374,173 of Critchley et al. and 3,424,683 of Dazzi et al. there are disclosed triazine and pyrimidine compounds. However, none of these patents discloses the linking of long chain or polymeric radicals to the heterocyclic groups.

U.S. Pat. No. 3,623,985 discloses trismonosuccinimides bonded to a triazine nucleus. The resulting compounds are stated to have detergent properties. These tri-monosuccinimido substituted triazines are not the same compounds as the tri-succinimido pyrimidines and triazines, nor the di-succinimido-amino-pyrimidines and triazines, nor the other substituted-triazines or pyrimidines of this invention.

SUMMARY OF THE INVENTION

A novel class of multifunctional additives for industrial solids and fluids are those in which one or more nitrogen-containing substituents are interlinked through basic nitrogen atoms to a heterocyclic nitrogen compound, the molecule containing from one to three occurrences of the bond group

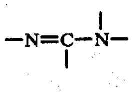

per heterocyclic ring in which the

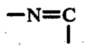

portion represents part of the heterocyclic group, and the

portion represents the bond between the said heterocyclic group and the nitrogen atom of an alkyl-amino or arylamino group or their derivatives or a group derived from an alkenylsuccinimide or an alkyl or alkenyl lactam or pyrrolidine, or a Mannich base.

DESCRIPTION OF SPECIFIC EMBODIMENTS

The additives of this invention have either of the following structures:

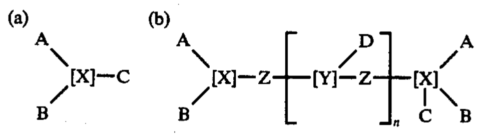

in which X and Y are each a heterocyclic radical derived from pyridine, diazine, (pyridazine, pyrimidine, pyrazine) or triazine, and may be the same or different in (b); Z is a divalent radical derived from ammonia, an amine, or a diamine, or higher polyamine; *n* is either 0 or an integer of at least 1, and preferably 1 to 10; and A, B, C, and D may each be hydrogen or alkyl, aralkyl, alkenyl, aryl, alkaryl, hydroxyalkyl, hydroxyaryl, carboxy, alkylcarboxy, hydroxy, phosphono, phosphato, sulfonato, mercapto or a nitrogen-containing substituent, the organic groups of A, B, C, and D having from 1 to about 500 carbon atoms, and preferably from 1 to about 100 carbon atoms; provided that at least one of A, B, C, or D is one of the nitrogen-containing substituents. Thus the said groups may be of lower molecular weight, such as methyl, ethyl, propyl, decyl, octadecyl, phenyl, tolyl, benzyl, and the like, or derived from polymers, such as polythylene, polypropylene, polybutene, polyvinyl, polystyrene, styrene, olefin copolymers and the like.

Collectively, the nitrogen-containing substituents referred to herein include alkyl-amino, arylamino, succinimide amino, lactam amino, and the like having the formula

wherein, R and R' may each be hydrogen, alkyl, aralkyl and hydroxyalkyl, aryl, hydroxyaryl, alkaryl, or one or both of R and R' is either an alkylene polyamino radical $—(C_mH_{2m}NH)_eH$, wherein *m* is an integer of from 1 to 3 and *e* is an integer of at least 1 and preferably may range from 1 to about 10, or an alkenylsuccinimide alkylene amino or alkyl lactam alkylene amino or alkyl pyrrolidine alkylene amino, such as

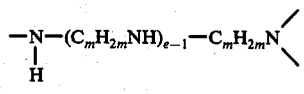 or

-continued

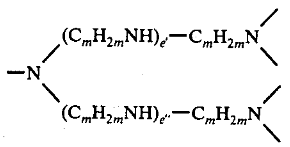

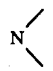

representing succinimide, lactam or pyrrolidine groups and the sum of $e'$ and $e''$ being from 0 to 10, or the alkylphenol methylene amino (i.e. Mannich bases of U.S. Pat. No. 3,368,972),

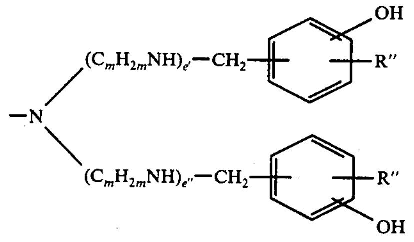

wherein R'' is preferably alkyl of at least 8 carbon atoms.

As indicated, each occurrence of X and Y in the (b)-type molecule may be the same or different, A, B, and C may be the same or different for each X group, and D may be the same or different for each $n$ number of Y groups.

The more preferred compounds of this invention are those having the following structures:

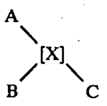

and

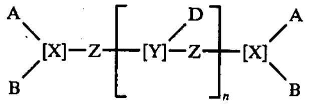

in which each X and Y is a pyridine, pyrimidine, or triazine; A, B, and C are amino, anilino, alkylamino, or alkylanilino having from 1 to more than 100 carbon atoms, e.g. imide amino, bis(imide)amino, lactam amino, or bis(lactam)amino, D may be one of these groups or hydrogen, and $n$ is 0 to 6; and Z is imino or alkylene polyamino. Preferably, at least one substituent on each X group consists of an amino group or an alkenylsuccinimide amino or bis(alkenylsuccinimide)amino group or an alkyl or alkenyl lactam or pyrrolidine amino or bis(alkyl or alkenyl lactam or pyrrolidine)amino group or an alkylsubstituted phenolmethylene amino or bis(-phenolmethylene)amino group, each having at least 8 carbon atoms in each alkyl or alkenyl radical and may range to over 10,000 carbon atoms, or combinations thereof. Preferably the alkenyl and alkyl groups of these preferred substituents contain from 8 to about 300 carbon atoms, and more particularly from 20 to 200 carbon atoms.

More specifically, the compounds of this invention may be prepared generally by reacting a halogenated heterocyclic compound, such as di- or trichloropyrimidine or cyanuric chloride, with the reactants necessary to supply the desired substituents, at least one of which is a basic nitrogen compound. To produce (b)-type compounds, ammonia and primary amines, diamines and higher polyamines are used to obtain additional heterocyclic linkages. This substitution reaction is preferably carried out at a temperature between 70° C. and 250° C. over a period of from 0.5 to 15 hours. To illustrate preparation of typical compounds of this invention using a chlorinated pyrimidine as the heterocyclic compound, one of the basic nitrogen atoms of an alkenylsuccinimide amine (the terminal nitrogen atom) having the structure

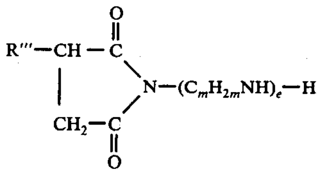

or a bis(alkenylsuccinimide)amine (one of the inner nitrogen atoms) having the structure

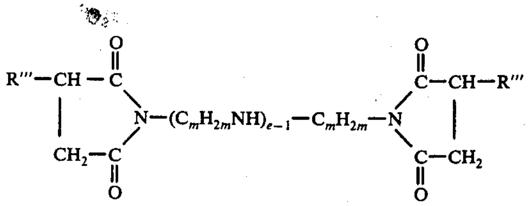

wherein R''' is an alkenyl group, $m$ an $e$ having the aforesaid definitions, becomes linked to the pyrimidine upon evolution of hydrogen chloride. The molar ratios of the two reactants may be varied to replace all of the chlorine atoms to produce the (a)-type compound. The corresponding alkyl lactam or bis(alkyl lactam)amines and other amino or anilino substituents may be added in a similar manner. Compounds having mixed substituents, for example, a mono-amino-di-succinimideamino pyrimidine, may be obtained by varying the amine-type reactant. One of the most preferred products of this invention consists of a pyrimidine or triazine ring substituted by three bis(polyalkenylsuccinimide)tetraethylene pentamine groups.

In order to obtain the (b)-type additive, at least one halogen atom is left after the desired substitution reactions. The substituted monohalo heterocyclic, such as a monochloro-dialkenylsuccinimideamino pyrimidine, is reacted with ammonia or a primary amine or preferably a polyalkylenepolyamine, $H_2N-(C_mH_{2m}NH)_eH$, such as the ethylene polyamines ($m=2$) ethylenediamine ($e=1$), diethylenetriamine ($e=2$), triethylenetetramine ($e=3$), tetraethylenepentamine ($e=4$), and the like. With a mole ratio of 2:1 of substituted pyrimidine to amine or polyamine, the reaction mixture is believed to contain the bis-(substituted pyrimidine) of the aforesaid (b)-type formula in which $n$ is 0. If the substituted monohalo heterocyclic is reacted with a preformed diamino or di(polyamino) heterocyclic compound in a 2:1 mole ratio, the final reaction product is understood to contain a tris-cyclic compound ($n$ is 1). Alternatively, by reacting one or two different substituted heterocyclic compounds containing an amino group attached with a dihalo heterocyclic compound, mixed tris-cyclic products can be prepared.

As may be seen, a great variety of interlinked products are obtained by changing these reaction sequences or using different heterocyclic and basic nitrogen reactants as desired. By repeating the amine connections of further substituted heterocyclic compounds, even more interlinked substituents can be attached to the molecule.

Thus, the resulting compounds may contain an exceedingly high molecular weight and possess excellent oil solubility, as well as additive activity. By the means of this invention additives having molecular weights of over 100,000 may be thus obtained.

In preparing the (b)-type compounds of this invention, it may be desirable to react the halogenated heterocyclic compound with one of the A, B, C, or D substituent precursors prior to reactions with the preferred polyamine providing the Z linkage, although it is not a critical requirement. For example, reaction of a trichloropyrimidine with ammonia or an amine or aniline or succinimide amine or lactam amino or pyrrolidine amine, or Mannich base compound would preferably precede reaction with the polyamine providing the Z linkage.

In another variation of this invention, instead of reacting the halogenated heterocyclic compound with a preformed alkenylsuccinimide or alkyl lactam, the heterocyclic is reacted with a polyamine having at least 2 primary amino groups, and the resulting heterocyclic-polyamine compound is then reacted with an alkenylsuccinic anhydride or a lactone, with the removal of a mole of water per mole of anhydride or lactone. The terminal primary amino group of the polyamine, being more basic than the internal nitrogen is believed to provide the imide or lactam. Amides are also formed. If the polyamine is terminated by a secondary amino group, the resulting product would be amide. On the other hand, reaction with a bis-alkenylsuccinimide amine or bis lactone amine reactant is believed to involve one of the inner basic nitrogen atoms. The actual structures of these final products are not entirely understood. The reaction sequence just discussed may be used for either the (a) or (b) type.

The preparation of the alkenylsuccinimide amines, alkyl lactam amines, alkyl pyrrolidine amines and alkyl-substituted Mannich bases is not part of this invention. The succinimides may be prepared by reactions first between olefins and maleic anhydrides, followed by reaction of the product with amines, as described, for example, in U.S. Pat. No. 3,172,892. Lactam amines can be prepared by the reaction between lactones and amines and the removal of water to yield the cyclic product. Pyrrolidines are prepared by the reduction of succinimides and lactams, U.S. Pat. No. 3,799,877, or by other known means. The Mannich bases may be prepared by the reaction of an alkylphenol, an aldehyde and an amine, as described in U.S. Pat. No. 3,368,972.

Our novel products may be treated by washing with water and/or solutions of organic and inorganic bases. Residual quantities of metal in the final product may improve the functioning of the product in the industrial fluid. We have found it more desirable to react the product with a metal reactant in the form of hydroxide, oxide, carbonate, carboxylate, alcoholate, or phenolate, or other basic substances which incorporate metal into the reaction product by heating. The nature of the final product is not known with certainty, however, it is believed that some or all of the succinimide rings may open to form a metal carboxylate salt of the succinamic acid. From about 0.005% to about 10% by weight of metal, alkali or alkaline earth metals, e.g., sodium, potassium, calcium, zinc, nickel or manganese in these products are beneficial.

The effectiveness of the compounds of this invention are believed to involve the presence of interlinked high molecular weight or polymeric compounds. The additional substituents such as amino, alkylamino, anilino and the like provide chemisorptive stable "anchor" groups in the polymeric structure. These groups are believed to permit strong adsorption to solid surfaces with which an industrial fluid medium may come in contact, including supersolids in the medium, giving these additives not only improved functionality but also greater stability at elevated temperatures. It has been found that detergent properties are enhanced by the interlinked structures of this invention. Moreoever, antioxidant properties assist the fluid medium in resisting high temperature deposit formation. These additives are also seen to provide a certain amount of antiwear properties and they have sufficient water and acid solubility to avert breakdown of the performance of the organic fluid. The additives of this invention may be used alone or in combination with other known additives usually used in formulation of industrial fluids.

The following examples are presented for the purpose of illustrating the preferred embodiments of this invention and are not considered to be a limitation of the scope thereof. The products produced in these examples are analyzed by gel permeation chromatography using Waters Associates Permeation Chromatograph, Model 200 operated at room temperature in benzene as solvent, using 50/80Å, 80/100Å (2), 350/700Å, and 700/2000Å columns. The procedure has been described in literature as for example, Journal of Chemical Ed., Volume 43, Page A567 (1966).

In these examples the essential ingredient may be referred to by structure or by name. The naming or depicting of these products is for convenience only in describing the type of molecule believed to be produced.

EXAMPLE 1

In a suitable reactor equipped with an agitator and condenser were added 18.2 grams (0.1 mole) of 2,4,6-trichloropyrimidine and 52 grams (0.2 mole) of dodecylaniline. The mixture was heated to 150° to 180° C. for 90 minutes during which period hydrogen chloride evolution ceased.

To the di(dodecylanilino)chloropyrimidine was added 20 grams (0.1 mole) of tetraethylenepentamine. The reaction mixture was heated to a temperature of 190° to 210° C. for 3 hours, then 135 grams (0.1 mole) polybutenylsuccinic anhydride, obtained by reacting a polybutene having a molecular weight of 1,350 with maleic anhydride, was added. The reaction mixture was stirred at 150° to 180° C. for 5 hours, during which time water condenses out. The reaction was stopped after 1½ hours at 150° C. under house vacuum and nitrogen atmosphere after water condensation ceased.

The yield of final reaction product was 170 grams containing a compound having the presumed structure,

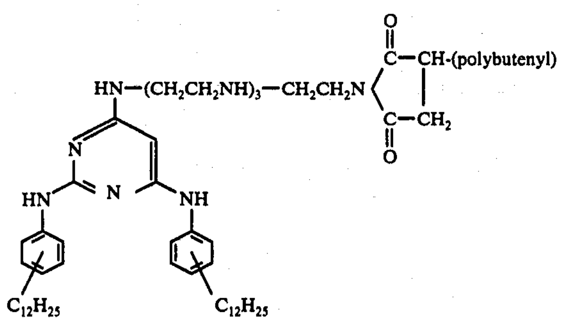

The product was dissolved in about 500 cc toluene and washed once with 50 cc 5% NaOH solution and twice with 500 cc $H_2O$. n-Butanol was used to break up the resulting emulsion. Upon distilling off the toluene-alcohol from the organic layer and holding the residue at 170° C. under house vacuum for 2 hours, the yield was 160 grams.

Found: %N, 4.25

The reaction mixture may also contain a minor amount of the corresponding half amide.

EXAMPLE 2

To the same apparatus used in Example 1 were added 30 grams (0.165 mole) of 2,4,6-trichloropyrimidine and 1050 grams (0.50 mole) of the bis-polybutenyl succinimide of tetraethylene pentamine, the polybutenyl groups having about 900 molecular weight. The reaction mixture was heated at 150° to 180°0 C. for 7 hours, cooled and dissolved in 1500 cc toluene and washed twice with 200 cc of 12.5% NaOH solution and twice with 250 cc distilled water; n-butanol was used to break emulsion during the washes. The washed material was distilled to 150° C. under vacuum and nitrogen for 2 hours. The yield of final reaction product was 940 grams (96% theoretical), a major component of which is believed to be 2,4,6-tri-substituted pyrimidine, the substituent obtained from the bis-succinimide reactant.

Found: %N, 2.26; %basic, N, 0.97; %Cl, 0.17

EXAMPLE 3

To a reactor were added 8.5 grams (0.05 mole) of 2-amino-4,6-dichloropyrimidine and 300 grams (0.1 mole) of the bis-polybutenylsuccinimide of Example 2. The reaction mixture was heated at 200° to 220° for 6 hours during which hydrogen chloride evalved. The resulting reaction mixture was treated as in Example 2. The yield of the remaining reaction product, believed to contain primarily the corresponding 4,6-di-substituted-2-aminopyrimidine, was 270 grams (96% of theoretical); this reaction product has the following analysis:

Found: %N, 2.36; %basic, N, 0.98; %Cl, 0.15

EXAMPLE 4

In a reactor similar to that of Example 1, 32 grams (0.2 mole) of a 2-amino-4,6-dichloropyrimidine was reacted with 550 grams (0.2 mole) of the bis-polybutenylsuccinimide of Example 2 at 170° C. for 2 hours. To the resulting product was added 20 grams (0.1 mole) of tetraethylene pentamine, and the mixture heated at 175° to 180° C. for a period of 5 hours. The reaction mixture was treated in the same manner as in Example 2. The yield of reaction product, containing primarily bis-substituted-pyrimidinylamine of the (b) type (in which *n* is O, A is $-NH_2$ and B is derived from the bis-succinimide), was 565 grams (over 96% of theory). The product has the following analysis:

Found: %N, 3.23; %basic N, 1.34; %Cl, 0.32

EXAMPLE 5

Using the same procedure as in Example 3, one mole of aminodichloro triazine, made by reacting cyanuric chloride with ammonia gas, is reacted with 2 moles of the bis-polybutenylsuccinimide reactant of Example 2. The resulting product, consisting primarily of an aminotriazine bearing two succinimide amino substituents, is obtained in the yield of 96% theoretical and has the following analysis:

Found: %N, 2.20; %basic N, 0.81

EXAMPLE 6

Using a similar procedure and reaction conditions as Example 5, one mole of aminodichlorotriazine is reacted with 2 moles of a bis-polybutenylsuccinimide of tetraethylenepentamine, in which the polybutenyl group is derived from polybutene having a molecular weight of 1,300. The substituted triazine yield is 95% theoretical and has the following analysis:

Found: %N, 3.3

EXAMPLE 7

In a suitable reactor, 8 grams of 2-amino-4,6-dichloropyrimidine (0.05 mole) were mixed with 75 grams of a process oil (a solvent-refined mineral oil) and 140 grams of bis-polybutenyl succinimide, (0.05 mole, molecular weight of polybutene being about 900) and heated at 160° to 170° C. for 5 hours. Then 4 grams (0.025 mole) of 2,6-diaminopyridine was added and heating continued at 170° to 180° for 16 hours. The product was processed as described in Example 2. The final product yield is 215 grams or 95% theory and essentially having the structure believed to be

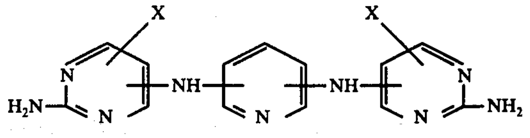

wherein X = bis(polybutenylsuccinimido)amino

Found: %N, 2.48; %basic N, 0.64; %Cl, 0.02

EXAMPLE 8

Using the same procedure as in Example 2, 1 mole of 2,4,6-trichloropyrimidine is mixed with 3 moles of a bis(alkyl-lactam) of tetraethylenene pentamine, wherein the alkyl groups are polybutyl groups having a molecular weight of about 900. The resulting product is believed to contain the corresponding tri-substituted pyrimidine.

EXAMPLE 9

Using the same procedure as in Example 2, 1 mole of 2-amino-4,6-dichloropyrimidine is reacted with 2 moles of the Mannich base (prepared by reacting a polypropylphenol having a molecular weight of about 900; tetraethylene pentamine and formalydhyde in a mole ratio of 2:1:2 respectively). The resulting product is believed to contain the corresponding aminopyrimidine disubstituted with the Mannich base.

EXAMPLE 10

In a suitable reactor, 9 grams of 2,4,6-trichloropyrimidine, 9 grams of N-phenyl-p-phenylene diamine, 5 grams of 2-(2-aminoethylamino)-ethanol and 140 grams of the bis-polybutenylsuccinimide of Example 2 were reacted under the conditions of Example 1. A yield of 135 grams of product was obtained.

Anal: Found: %N, 3.31; %Cl, 0.05

EXAMPLE 11

Using the same conditions as in Example 10, 16 grams of 2-amino-4,6-dichloropyrimidine, 18 grams of the said diamine and 280 grams of the succinimide were reacted together. A yield of 308 grams of product was obtained.

Anal: Found: %N, 3.89; %Cl, 0.03

EXAMPLE 12

Using the same conditions as in Example 2, 35 grams of 2,6-diamino-4-chloropyrimidine and 600 grams of the bis-succinimide of Example 2 were reacted in the presence of 200 grams of a process mineral oil; 772 grams of total reaction mixture was obtained.

Anal: Found: %N, 2.55; %Cl, 0.08

EXAMPLE 13

Using the procedure of Example 10, 35 grams of 2-amino-4 chloro-6-methylpyrimidine and 600 grams of the bis-succinimide of Example 2 were reacted in the presence of 200 grams of process mineral oil; 795 grams of total reaction mixture was obtained.

Anal: Found: %N, 2.35; %Cl, 0.16

EXAMPLE 14

Using reaction conditions of Example 1, 2264 grams of the bis-succinimide of Example 2, 200 grams of dodecyl aniline and 80 grams of cyanuric chloride were reacted in 900 grams of process oil. The yield of reaction mixture was 3189 grams. It is believed that the schematic structure of the active ingredient is:

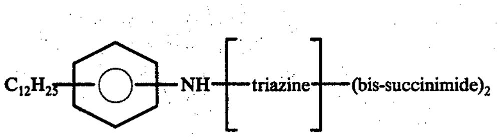

EXAMPLE 15

In a suitable reactor, 10.8 grams of cyanuric choride dissolved in 100 cc of dimethylformamide (DMF) was reacted with 2.7 grams of ethylenediamine dissolved in 100 cc of DMF by mixing the reactant solutions together and held for from 10 to 30 minutes. To the resulting product mixture was added 160 grams of the bis-succinimide of Example 2. DMF was removed by distillation and 60 grams of process mineral oil was added to the mixture. The reaction continued at about 180° C. for 8 hours. The reaction product was processed as in Example 2. The yield of product was 145 grams.

Anal: Found: %N, 1.02; %Cl, 0.3

It is believed that a component of the reaction product has the following structure $X_2$-[triazine-]$NHCH_2CH_2NH$-[triazine-]$NHCH_2CH_2NH$-[triazine-]$X_2$
X wherein X is the bis-succinimideamino group derived from the bis-succinimide reactant.

EXAMPLE 16

In a suitable reactor, 1.6 grams of 2-amino-4,6-dichloropyrimidine and 210 grams of a bis-polybutenylsuccinimide similar to that of Example 2, except that the polybutenyl groups are derived from a polybutene having a molecular weight of 2300, are reacted in the presence of 20 grams of process mineral oil under the conditions of Example 2. The product mixture weighed 185 grams.

Anal: Found: %N, 0.72; %Cl, 0.01

EXAMPLE 17

In a suitable reactor, 40 grams of 2,6-dichloropyridine and 1350 grams of the bis-succinimide of Example 2 were reacted in 270 grams of process mineral oil at about 200° C. for 12 hours under nitrogen atmosphere. As a catalyst, about 40 grams of sodium carbonate was present. The product was treated as in Example 1, leaving 1050 grams of product, consisting to a great extent of the structure,

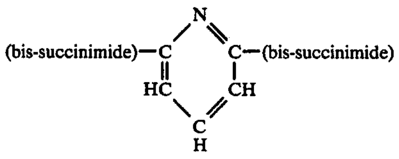

Anal: Found %N 1.62

The reaction can be carried out in an autoclave at higher temperatures, eg 240°-260° C., under nitrogen pressure to give higher yields of the products.

EXAMPLE 18

The product of Example 12 (%N, 2.55; %Cl, 0.08; %Na, 0.08) was reacted with sodium hydroxide as follows: 250 grams of the Example 12 product was mixed with 20 cc of a water solution containing 1.5 grams NaOH, 50 cc of 2-propanol and 500 cc of benzene. The benzene-water-propanol liquids are removed by distillation and the reaction mixture is heated to 170° C. and held at that temperature under house vacuum for 1½ hours. The resulting product was filtered leaving 240 grams of liquid product.

Anal: Found: %N, 2.51; %Na 0.37

EXAMPLE 19

The final product of Example 2 (200 grams) is reacted with 2 grams of NaOH dissolved in 10 cc of water in the presence of a solvent consisting of 50 cc of 2-propanol and 100 cc of toluene, under the conditions of Example 18. The yield of product was quantitative.

Anal: Found: %Na, 0.55

EXAMPLE 20

In a suitable reactor, 23.5 grams of a product prepared as in Example 2, but containing 0.41% sodium, is reacted with 4 cc of a solution of 50% by weight sodium hydroxide in water. The reaction is carried out in the presence of 40 grams of a process mineral oil, 40 cc of xylene and 10 cc of 2-propanol as in Example 18. The yield of product was 29 grams.

Anal: Found: %N, 1.68; %Na, 0.99

EXAMPLE 21

A mixture of 1342 grams of the product of Example 20 (0.41% Na), 220 grams of zinc acetate, 200 cc of water, 120 grams of process mineral oil and 100 cc of 2-propanol was slowly heated to reflux. The water and propanol were allowed to distill off. Heating was continued at 160° to 170° C. for 2 hours under house vacuum. The yield of product after filtration was 1250 grams.

Anal: Found: %N, 1.80; %Na, 0.31, %Zn, 2.05; %Cl, 0.05

EXAMPLE 22

COMPARISON EXAMPLES

Following the procedure of the disclosure of U.S. Pat. No. 3,623,985, two products were prepared as follows:

(a) One mole of tetraethlenepentamine was reacted with one mole of polybutenylsuccinic anhydride obtained from a polybutene having a molecular weight of about 900 and maleic anhydride, 3 moles of the resulting product was reacted with 1 mole of cyanuric chloride. The product was washed with sodium bicarbonate solution and then with water.

(b) The same conditions and procedure as in (a) were followed, except the polybutene precursor had a molecular weight of 1350.

Two further examples show the reaction of substituted triazines with sodium hydroxide.

EXAMPLE 23

In a suitable reactor, 100 grams of the product of Example 6 is reacted with 2 cc of a solution of 50% by weight of sodium hydroxide in water. The reaction is carried out by heating the above in solvent mixture consisting of 50 cc toluene and 50 cc isopropyl alcohol to remove all the toluene-$H_2O$-alchol overhead and the holding residue at 170° C. under house vacuum for 1½ hours and filtering.

Anal: Found: %N, 3.5; %Na, 0.52

EXAMPLE 24

One mole of cyanuric chloride is reacted with 3 moles of the polybutenylsuccinimide of Example 2 under the conditions of Example 2, to produce the corresponding trisubstituted triazine. The resulting product (100 grams) was reacted with 4 cc of the sodium hydroxide solution under the same conditions as in Example 23. The yield of product was quantitative.

Anal: Found: %N, 2.36; %Na, 0.98

It should be noted that the reaction products of this invention as illustrated by the above examples may have one or more heterocyclic nitrogen compounds having utility. The structures or nomenclature used herein are believed to be representative of the major component. There are also believed to be other components, which may not be susceptible to identification, present in the final reaction product and which also provide desired useful functions.

EVALUATION OF PRODUCTS

The additives of this invention are tested in a series of tests to indicate their utility in lubricating oils.

1. The sulfuric acid and pyruvic acid tests indicative of detergent properties are described in U.S. Pat. No. 3,368,972. The test oil consists of a blend of solvent refined mineral oils (SUV at 210° F. of 64.1) 1% by weight of a zinc dialkyl phosphorodithioate. To the oil is added 3% by weight of a compound of this invention. In the sulfuric acid test, the lower the result the better the additive. In the pyruvic acid test, the higher the result the better the additive. The following results are obtained:

| Test Oil | Sulfuric Acid Test | Pyruvic Acid Test (%) |
|---|---|---|
| Alone | 0.102 | 58.6 |
| Example 1 Product | 0.002 | 99.6 |
| Example 2 Product | 0.006 | 99.9 |
| Example 3 Product | 0.004 | 99.9 |
| Example 4 Product | 0.004 | 99.9 |

2. The compounds of this invention have also been tested as lubricant additives in oxidation stability or antioxidant tests. The test procedure consists of mixing air, flowing at a controlled rate, with a second controlled flow stream of nitrogen oxides and sulfur dioxide in a mixing tank. The gas mixture is saturated with water by passing it through a fritted glass bubbler and then through a pre-heater. The heated stream is introduced into a reactor at a controlled rate. Samples of test oil blends (similar to that used in the previous test except the SUV at 120° F. is 86.1) containing compounds of this invention are also pre-heated and pumped into an oil reservoir of the reactor. An aluminum shaft, equipped to rotate at constant speed, is immersed in the oil reservoir while a portion thereof is exposed to the water-air-gas mixture. The shaft is maintained at a temperature of about 575° F. Thus, the oil from the reservoir coats the shaft as it rotates and becomes exposed to the upper portion of the reaction chamber filled with air and oil vapor as a thin film. The duration of the test is 70 minutes.

The rating of this test is based on the amount of oil oxidation-degradation products, such as lacquer, which become deposited on the aluminum surface of the shaft. The rating is made visually by classifying the deposits as follows: 1 indicates a clean aluminum surface or extremely light deposit; 2, moderately light or iridescent surface; 3, light or golden deposit and transparent; 4, medium or brown and translucent; 5, heavy or brown and opaque; and 6, very heavy black or brown and rough. The results are:

| Oil Composition | Concentration By Weight | Rating |
|---|---|---|
| oil blend | 0 | 4.0, 4.3, 3.7 |
| bis-succinimide reactant used in Example 2 | 10% | 4.5 |
| Example 2 Product | 5% | 1.0, 1.1 |
| Example 3 Product | 5% | 1.0 |
| Example 4 Product | 5% | 1.0 |
| Example 5 Product | 6% | 1.3 |
| Example 22 (a) Product | 5% | 5.2 |
| Example 22 (b) Product | 5% | 5.0 |
| Example 23 Product | 5% | 1.3 |
| Example 24 Product | 5% | 1.0 |

3. An oil containing the bis-pyrimidine compound of Example 4 is tested in a standard 4-ball wear test. In this test 3 steel balls of 52-200 steel are held in place in a ball cup. A fourth ball positioned on a vertical spindle is brought into contact with the three balls and rotated against them. The force with which the fourth ball is held against the three stationary balls may be varied as desired. The test lubricant is added to the ball cup and acts as the lubricant for the rotation.

At the end of the test, the steel balls are removed and investigated for wear scar. The extent of scarring represents the effectiveness of the product as an antiwear agent; little or no scarring indicates an excellent antiwear agent. In the following series of test, loads of 40 and 60 kilograms are used for a duration of ½ hour at oil temperatures of 300°, 400°, and 550° F., and the rotational speed of the ball is 600 r.p.m. or 23.3 cm/sec. sliding speed. The oil medium is the same mineral oil blend used in the sulfuric and pyruvic acid tests. The additive concentration is 5% by weight.

| | Wear Scar Diameter (mm) | | | |
|---|---|---|---|---|
| | 40 kilograms | | | 80 kilograms |
| Lubricant Composition | 300° | 400° | 500° F | 300° F |
| Alone | 0.745 | 0.785 | 0.895 | 0.908 |
| Example 4 Product | 0.531 | 0.690 | 0.844 | 0.807 |

4. The composition of Example 3 is tested in the Caterpillar 1-G Engine Test. The oil composition used in the test consists of the same mineral oil blend used in the sulfuric acid and pyruvic acid tests, containing 1.3% magnesium alkyl benzene sulfonate, 1.2% of a zinc dialkyl phosphorodithioate, 1.0% of barium phosphosulfonate of polypropylene and 2.5% of the product produced in Example 3. The test engine is a single cylinder, 4-cycle Caterpillar engine operated under the following conditions:

| | |
|---|---|
| Speed, r.p.m. | 1000 |
| Brake load, HP | 19.8 |
| Oil temperature, ° F | 150 |
| Jacket temperature, ° F | 150 |
| Fuel | Diesel fuel containing 1% sulfur |

The engine is operated for 480 hours, ratings are made periodically. These ratings consist of: piston deposits (100% is clean), lacquer demerits (0 is clean) and percent top groove packing deposits (0 is clean). The following results are obtained:

| | | | |
|---|---|---|---|
| Time, hours | 120 | 240 | 480 |
| Piston rating | 90.9 | 90.2 | 82 |
| Lacquer demerits | 3.7 | 4.3 | 9.6 |
| Top groove | 69.0 | 68.0 | 92.0 |

Using the same lubricant formulation but with the bis-polybutenylsuccinimide reactant of Example 3 instead of the final product, the piston rating after 120 hours is 84; after 240 hours, 68. The lacquer demerits are 9.6 and 21.4; top groove packing 35 and 51, both for 120 and 240 hours, respectively.

5. The product of Example 1 is tested in an oxidation test on an ester lubricant prepared from a pentaerythritol esterified with 5-carbon and 9-carbon carboxylic acids. The concentration of the compound is 2 percent by weight. The test oil is subjected to a stream of oxygen at temperatures of 425° C. and 450° C. in the presence of iron, copper, lead and aluminum. The test is carried on for 24 hours. The air flow rate is about 10 liters per hour. The lead sample is weighed before and after the test since lead is one of the more susceptible metals to corrosion by oxidation. The test measurements are lead loss in milligrams, neutralization number measured by ASTM D-974 (NN) and kinematic viscosity change (KV) at 210° F.

| Test Sample | NN | KV Increase Percent | Lead Loss mg |
|---|---|---|---|
| oil alone | | | |
| 425° F. | 8.25 | 422 | 13.8 |
| 450° F. | 10.15 | 1280 | 19.4 |
| oil plus Example 1 Product | | | |
| 425° F. | 0.45 | 73 | 4.4 |
| 450° F. | 1.62 | 86 | 14.4 |

6. The products of this invention are tested in hydrocarbon solution of various concentrations to determine its ability to solubilize water. This feature is of interest particularly in systems using industrial fluids in which water is likely to be present and have adverse effects on the working properties of the fluid. For the purpose of these tests, benzene or normal octane or mineral oil are used. An organic solution with the additive sample is mixed with water and agitated by shaking for a period of 24 hours. The water phase is then separated by centrifuge with at least 6,000 gravities for over ½ hour. The water content in the hydrocarbon phase is determined by Karl Fischer analysis. An oil blend similar to that of test 2, containing 5% by weight of the additive sample, is mixed with normal octane on a 1:1 basis. A sample of this blend is mixed with an equal volume of water. At the end of the agitation and separation steps, the following amounts of water determined by Karl Fischer analysis in the organic phase are:

| Additive | Percent Water By Weight | Moles Water per Mole Nitrogen |
|---|---|---|
| Example 2 Product | 1.00 | 6.2 |
| Example 3 Product | 0.41 | 2.6 |
| Succinimide Reactant of Example 2 | 0.05 | 0.18 |

This test indicates that the products of this invention provide improved ability over a known lubricating oil additive to solubilize water without producing emulsification of the oil or otherwise reducing its effectiveness as a lubricant.

7. This test indicates the ability of an oil additive to pick up and disperse particles in the oil, such as carbon particles.

A stainless steel cylindrical cell is mounted in a constant temperature both maintained at 100° C. Inside the cell is a 400-mesh nickel screen in which nickel powder has been placed as a porous bed. Carbon black is deposited on the bed by passing through the bed 10 cc of a dispersion of 250 ppm of carbon black in white oil at 1cc/min-, followed by 5cc of white oil alone. A solution of a solvent-refined mineral oil containing 5% by weight of active dispersant ingredient is passed through the bed at 1cc/min. Light transmission measurements of the oil composition before and after passage through the bed conform to Beer-Lambert, indicating the amount of carbon black removed from the bed. Two oil solutions were so tested. The results were as follows:

| DISPERSANT | PERCENT CARBON REMOVED |
|---|---|
| Product of Example 22 (b) | 25 |
| Product of Example 23 | 35 |
| Product of Example 24 | 39-40 |

The carbon removal test was followed in the evaluation of a fully formulated oil composition containing about 2% by weight of the active ingredient. Other additives in the oil include zinc dialkyl phosphorodithioate and metal sulfonates. These additives, as seen in the following results, provide little or no carbon dispersing properties in this test.

| DISPERSANT | PERCENT CARBON REMOVED |
|---|---|
| Oil Blend Alone | 1 |
| Product of Example 22 (a) | 15 |
| Product of Example 24 | 25 |

It can thus be seen that the compounds of this invention including those reacted with metal compounds, particularly sodium hydroxide, provide a number of different useful functions for industrial fluids such as liquid lubricants and greases. These additives may also be used in fuels, automatic transmission fluids, heat exchange fluids, metal working lubricants and coolants and resins, plastics, paints, coatings, etc.

The scope of this invention in the light of the preceding discription is intended to include all obvious modifications of said description except as limited in the following claims.

We claim:

1. A heterocyclic nitrogen compound selected from the class consisting of (a) a compound comprising two monovalent amine substituted mononuclear diazine nuclei in which each said monovalent amine substituent is bonded through an amino nitrogen atom to a carbon atom of one of said diazine nuclei, said diazine nuclei being linked one to the other through a bivalent amine radical bonded through an amino nitrogen atom to a carbon atom of each of said diazine nuclei;

(b) a monovalent amine substituted mononuclear diazine in which said monovalent amine substituent is bonded through an amino nitrogen atom to a carbon atom of the diazine nucleus, the amine of said monovalent amine substituent being selected from the group consisting of:

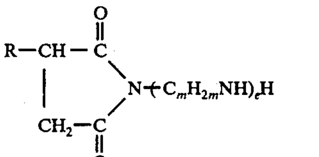
(1)

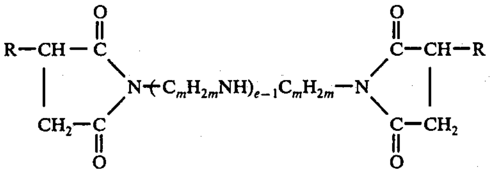
(2)

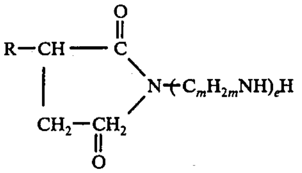
(3)

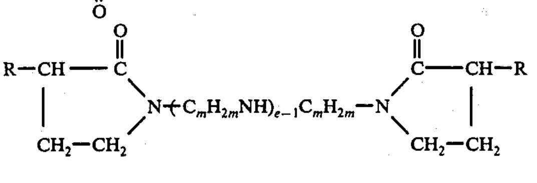
(4)

-continued

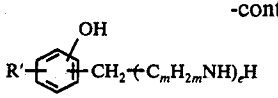
(5)

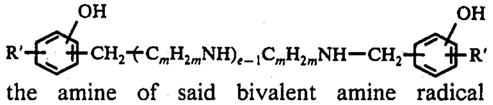
(6)

the amine of said bivalent amine radical being selected from the group consisting of $H_2N(C_mH_{2m}NH)_eH$ and (7)

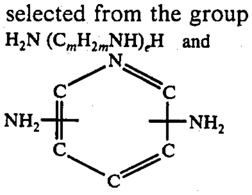
(8)

wherein:

*m* is an integer of from 1 to 3;

*e* is an integer of from 1 to 10;

R is an alkenyl group containing from 8 to about 300 carbon atoms; and

R' is an alkyl group containing from 8 to about 300 carbon atoms.

2. The compound of claim 1 in which said heterocyclic nitrogen compound also includes at least one additional substituent bonded to a carbon atom of at least one of said diazine nuclei, said additional substituent being selected from the group consisting of (a) amino, anilino, alkyl amino and alkyl anilino radicals having from 1 to 100 carbon atoms bonded directly through an amino nitrogen to a carbon atom of at least one of said diazine nuclei; (b) N-phenyl-p-phenylene diamine; (c) 2-(2-aminoethylamino)-ethanol and (d) an alkyl group having from 1 to 100 carbon atoms.

3. The compound of claim 1 in which each of the diazine nuclei of compound (a) also includes at least one additional amine substituent bonded directly through an amino nitrogen to a carbon atom of each said diazine nucleus, said additional amine substituent selected from the group consisting of members (1) through (6) inclusive, as defined in claim 1.

4. The compound of claim 1 in which the diazine nucleus is pyrimidine.

5. The compound of claim 1 in which the diazine nucleus is pyrimidine and in which the amine of said monovalent and said bivalent amine radicals is a bis(alkenylsuccinimide)amine having the structure of member (2) of the group of amines defined in claim 1.

6. The compound of claim 1 in which the diazine nucleus is pyrimidine including an additional monovalent amine substituent bonded through an amino nitrogen to a carbon atom of said pyrimidine nucleus, the additional monovalent amine of said monovalent amine radical havig the structure of member (1) of the group of amines defined in claim 1.

7. A compound comprising the compound of claim 1 which has been reactively combined with from 0.005% to about 10% by weight, based upon the total weight of said composition, of an alkali or alkaline earth metal.

8. The compound of claim 7 including of from 0.005% to about 1% by weight of said metal.

9. A compound comprising a product of the reaction of the compound of claim 1 and an alkali or alkaline earth metal oxide, hydroxide, carbonate, carboxylate, alcoholate or phenolate.

10. A compound of the formula

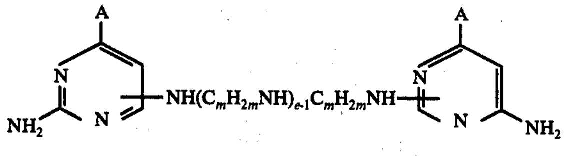

where A is a monovalent amine radical bonded through an amino nitrogen to a carbon atom of the pyrimidine nucleus, the amine of said monovalent amine radical having the structure

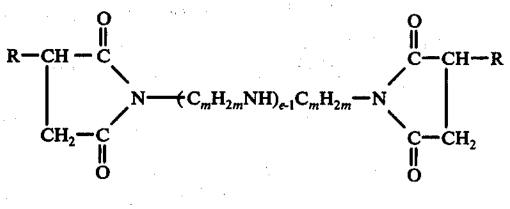

wherein:
- *m* is an integer from 1 to 3;
- *e* is an integer from 1 to 10; and
- R is an alkenyl group containing from 8 to about 300 carbon atoms.

11. A compound of the formula

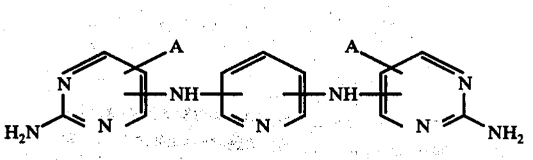

where A is a monovalent amine radical bonded through an amino nitrogen to a carbon of the pyrimidine nucleus, the amine of said monovalent amine radical having the structure of

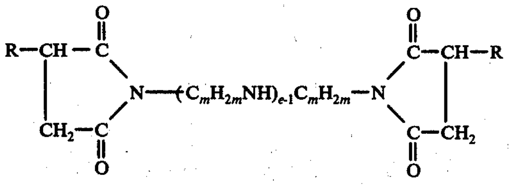

wherein:
- *m* is an integer from 1 to 3;
- *e* is an integer from 1 to 10; and
- R is an alkenyl group containing from 8 to about 300 carbon atoms.

12. A compound of the formula

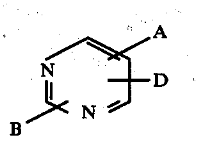

wherein A is a monovalent amine radical bonded through an amino nitrogen atom to a carbon atom of the pyrimidine nucleus, the amine of said monovalent amine radical being selected from the group consisting of

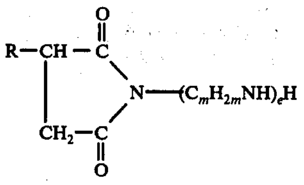 (1)

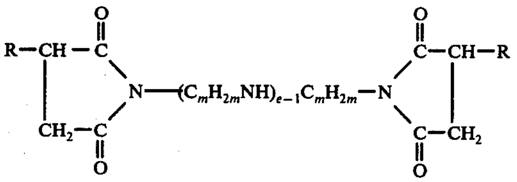 (2)

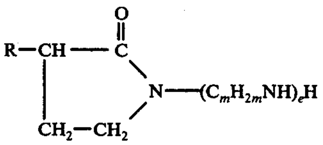 (3)

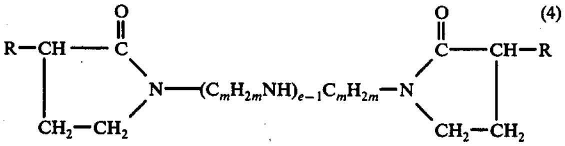 (4)

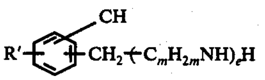 (5)

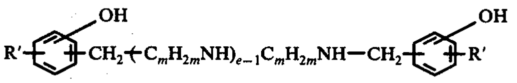 (6)

wherein:
- *m* is an integer from 1 to 3;
- *e* is an integer of from 1 to 10;
- R is an alkenyl group containing from 8 to about 300 carbon atoms;
- R' is an alkyl group containing from 8 to about 300 carbon atoms, and
- B and D are members selected from the group consisting of (a) hydrogen; (b) A; (c) amino, anilino, alkyl amino and alkyl anilino radicals having from 1 to 100 carbon atoms; (d) N-phenyl-p-phenylene diamine; (e) 2-(2-aminoethylamino)-ethanol, and (f) an alkyl group having from 1 to 100 carbon atoms.

13. The compound of claim 12 having the structure

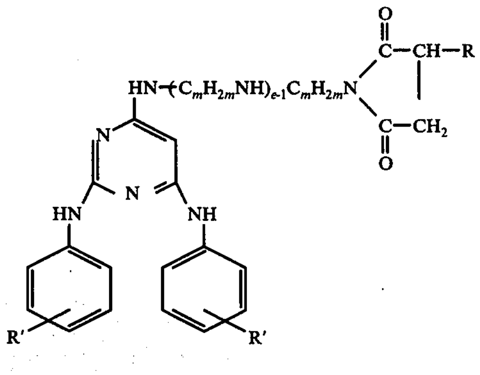

wherein
- *n* is an integer from 1 to 3;
- *e* is an integer from 1 to 10;

R is a polybutenyl group; and

R' is an alkyl group having up to 100 carbon atoms.

14. The compound of claim 12 having the structure

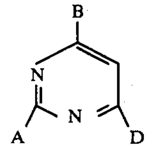

where A, B and D are monovalent amine radicals bonded through an amino nitrogen to a carbon atom of the pyrimidine nucleus, the amine of each said monovalent amine radical having the structure of member (2) of the group of amines defined in claim 12.

15. A compound comprising the compound of claim 14 which has been reactively combined with from 0.005% to about 1% of an alkali metal.

16. The compound of claim 12 having the structure

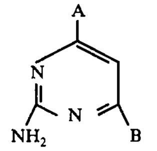

where B is an amino group and A is a monovalent amine radical bonded through an amino nitrogen to a carbon atom of the pyrimidine nucleus, the amine of said monovalent amine radical having the structure of member (2) of the group of amines defined in claim 12.

17. A compound comprising the compound of claim 16 which has been reactively combined with from 0.005% to about 1% of an alkali metal.

18. The compound of claim 12 having the structure

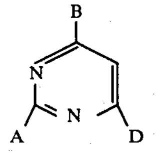

where A, B and D are monovalent amine radicals bonded through an amino nitrogen to a carbon atom of the pyrimidine nucleus, the amine of each said monovalent amine radical having the structure of member (4) of the group of amines defined in claim 12.

19. The compound of claim 12 having the structure

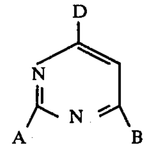

where A, B and D are monovalent amine radicals bonded through an amino nitrogen to a carbon atom of the pyrimidine nucleus, the amine of each said monovalent amine radical having the structure of member (6) of the group of amines defined in claim 12.

20. The compound of claim 12 having the structure

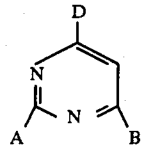

wherein A, B and D are monovalent amine radicals bonded through an amino nitrogen to a carbon atom of the pyrimidine ring, the amines of said monovalent amine radicals being selected from the group consisting of N-phenyl-p-phenylene diamine 2-(2-aminoethylamino)-ethanol, and an amine having the structure of member (2) of the group of amines defined in claim 12.

21. The compound of claim 12 having the structure

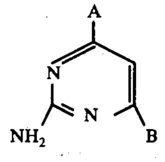

where

A is a monovalent amine radical bonded through an amino nitrogen to a carbon atom of the pyrimidine nucleus, the amine of said monovalent amine radical having the structure of member (2) of the group of amines defined in claim 12;

B is $NH_2$or a monovalent amine radical bonded through an amine nitrogen to a carbon atom of the pyrimidine ring, the amine of said amine radical being N-phenyl-p-phenylene diamine.

22. The compound of claim 12 having the structure

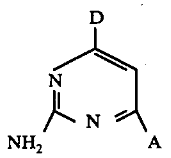

where

D is an alkyl group having from 1 to 100 carbon atoms, and A is a monovalent amine radical bonded through an amino nitrogen to a compound atom of the pyrimidine nucleus, the amine of said monovalent amine radical having the structure of member (2) of the group of amines defined in claim 12.

23. A compound of the formula

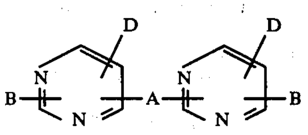

wherein

B is a monovalent amine radical bonded through an amino nitrogen atom to a carbon atom of each of said pyrimidine nuclei, the amine of said monovalent amine radical being selected from the group consisting of:

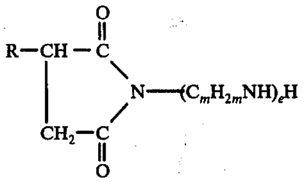
(1)

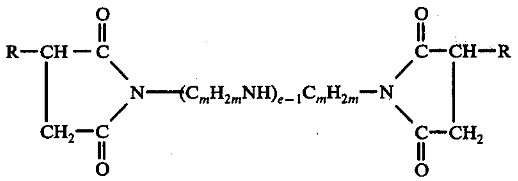
(2)

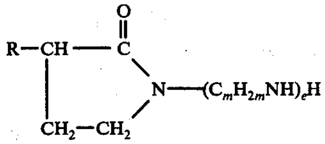
(3)

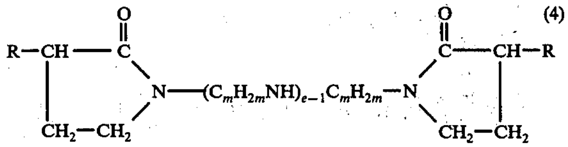
(4)

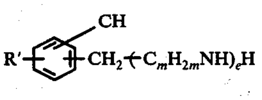
(5)

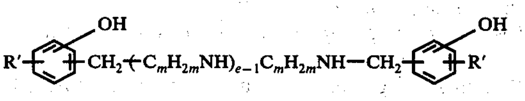
(6)

D is selected from the group consisting of (a) hydrogen; (b) a monovalent amine radical substituent bonded through an amino nitrogen atom to a carbon atom of the pyrimidine nucleus, the amine of said monovalent amine raidical being selected from the group consisting of members (1) through (6) inclusive of the group of amines defined above; (c) amino, anilino, alkyl amino and alkyl anilino radicals having from 1 to 100 carbon atoms; (d) N-phenyl-p-phenylene diamine; (e) 2-(2-aminoethylamino)-ethanol, and (f) an alkyl group having from 1 to 100 carbon atoms A is selected from the group consisting of (7) —HN $(C_mH_{2m}NH)_{e-1}C_mH_{2m}$ NH and

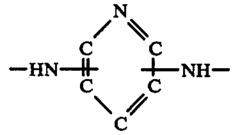
(8)

wherein:

*m* is an integer of from 1 to 3;

*e* is an integer of from 1 to 10;

R is an alkenyl group containing from 8 to about 300 carbon atoms; and

R' is an alkyl group containing from 8 to about 300 carbon atoms.

24. A compound of the formula

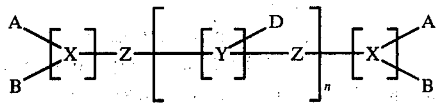

wherein X and Y are mononuclear diazine nuclei, Z is a bivalent amine radical connected through an amino nitrogen to a carbon atom of each of diazine nuclei to which said Z is bonded, the amine of said bivalent amine radical being selected from the group consisting of:

$H_2N\ (C_mH_{2m}NH)_eH$ and

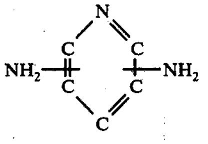

A is a monovalent amine substituent bonded through an amino nitrogen to a carbon atom of X, the amine of said monovalent amine substituent being selected from the group consisting of

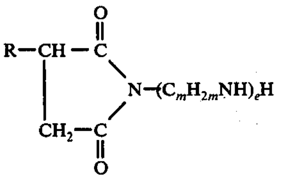
(1)

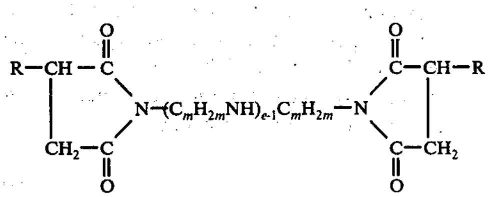
(2)

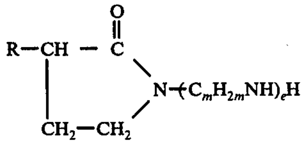
(3)

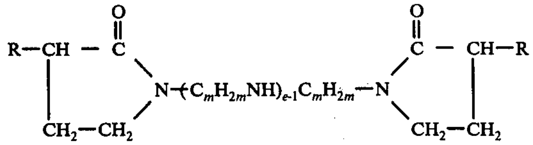
(4)

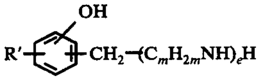
(5)

and

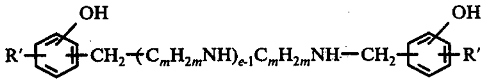
(6)

wherein:

*n* is from 0 to 10

*m* is an integer of from 1 to 3;

*e* is an integer of from 1 to 10;

R is an alkenyl group containing from 8 to about 300 carbon atoms;

R' is an alkyl group containing from 8 to about 300 carbon atoms, and

B and D are selected from the group consisting of (a) hydrogen; (b) A; (c) alkyl, alkenyl, hydroxyalkyl, and alkyl carboxy radicals having from one to about 500 carbon atoms; (d) aralkyl, aryl, alkaryl and hydroxyaryl radicals having from 1 to about 100 carbon atoms; (e) carboxy, hydroxy, phosphono phosphato sulfonoto and mercapto radicals; (f) N-phenyl-p-phenylene diamine; (g) 2-(a-aminoethylamino)-ethanol.

25. A compound of the formula

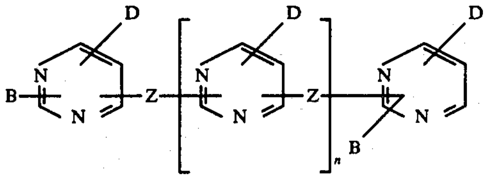

wherein Z is a bivalent amine radical bonded through an amino nitrogen to a carbon atom of each of said heterocyclic nuclei, the amine of said bivalent amine radical being selected from the group consisting of $H_2N(C_mH_{2m}NH)_eH$ and

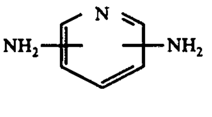

B is a monovalent amine substituent bonded through an amino nitrogen atom to a carbon atom of the pyrimidine nucleus to which B is bonded, the amine of said monovalent amine substituent being selected from the group consisting of:

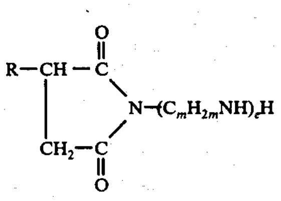

(1)

-continued

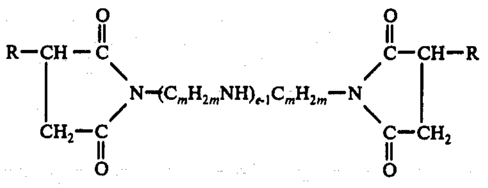

(2)

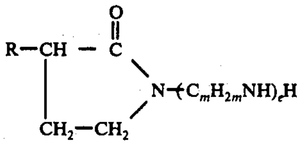

(3)

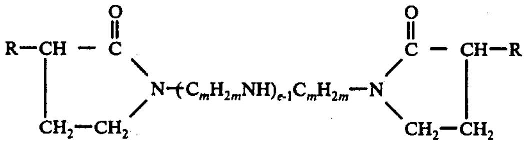

(4)

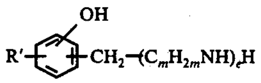

and (5)

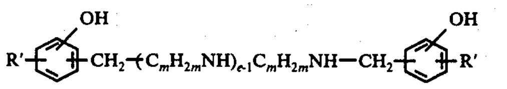

(6)

wherein:

$n$ is from 0 to 10;

$m$ is an integer of from 1 to 3;

$e$ is an integer of from 1 to 10;

R is an alkenyl group containing from 8 to about 300 carbon atoms; and

R' is an alkyl group containing from 8 to about 300 carbon atoms,

D is selected from the group consisting (a) hydrogen (b) B; (c) alkyl, alkenyl, hydroxyalkyl and alkyl carboxy radicals having from 1 to about 100 carbon atoms; (d) aralkyl, aryl, alkaryl and hydroxyaryl radicals having from 1 to about 100 carbon atoms; (e) carboxy, hydroxy, phosphono, phosphato, sulfonato and mercapto radicals; (f) N-phenyl-p phenylene diamine; and (g) 2-(a-aminoethylamino)-ethanol.

* * * * *

UNITED STATES PATENT AND TRADEMARK OFFICE
CERTIFICATE OF CORRECTION

PATENT NO. : 4,113,725

DATED : September 12, 1978

INVENTOR(S) : JOHN C. NNADI
ISRAEL J. HEILWEIL

It is certified that error appears in the above-identified patent and that said Letters Patent are hereby corrected as shown below:

[57] Abstract, formula (b) " 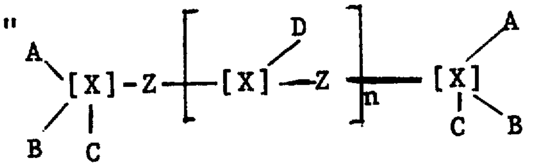 "

should read

-- 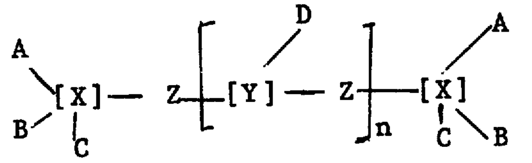 --

Col. 15, line 63, claim 1, formula (3)

"$CH_2 - \underset{O}{\underset{\|}{C}}H_2$" should read --$CH_2 - CH_2$--

Col. 17, line 5 (end of formula) " .... 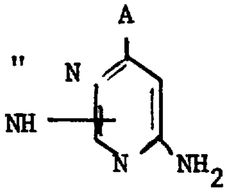 "

should read -- ..... 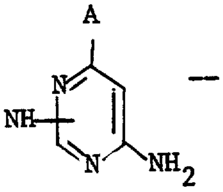 --

UNITED STATES PATENT AND TRADEMARK OFFICE

CERTIFICATE OF CORRECTION

PATENT NO. : 4,113,725

DATED : September 12, 1978

INVENTOR(S) : JOHN C. NNADI
ISRAEL J. HEILWEIL

It is certified that error appears in the above-identified patent and that said Letters Patent are hereby corrected as shown below:

Col. 21, line 42 : "raidical" should read --radical--

Signed and Sealed this

*Nineteenth* Day of *December 1978*

[SEAL]

*Attest:*

RUTH C. MASON
*Attesting Officer*

DONALD W. BANNER
*Commissioner of Patents and Trademarks*